United States Patent [19]

Smith

[11] Patent Number: 4,561,307

[45] Date of Patent: Dec. 31, 1985

[54] LIQUID DIFFERENTIAL PRESSURE MEASUREMENT USING A VERTICAL MANIFOLD

[76] Inventor: George E. Smith, 2115 S. Fountain Valley Dr., Missouri City, Tex. 77459

[21] Appl. No.: 574,035

[22] Filed: Jan. 26, 1984

[51] Int. Cl.⁴ .............................................. G01N 9/26
[52] U.S. Cl. ........................................ 73/438; 73/719
[58] Field of Search ................. 73/438, 299, 701, 716, 73/717, 719

[56] References Cited

U.S. PATENT DOCUMENTS

| | | | |
|---|---|---|---|
| 1,603,162 | 10/1926 | Star | 73/716 |
| 3,161,051 | 12/1964 | Perry | 73/299 |
| 4,128,013 | 12/1978 | Perry | 73/701 |
| 4,136,567 | 1/1979 | Rosenblum | 73/438 |

Primary Examiner—S. Clement Swisher
Assistant Examiner—John E. Chapman, Jr.
Attorney, Agent, or Firm—Vaden, Eickenroht, Thompson & Jamison

[57] ABSTRACT

Liquid differential pressure measurement apparatus using at each of two separate vertical locations a manifold with a pair of voids, each pair being covered with a thin, non-elastomer membrane pressing tightly against a horizontal fence line therebetween. A first void of each pair is gas pressurized from the external side of the manifold to move the membrane on the internal side of the manifold outwardly against the pressure head of liquid on the membrane at the location of the fence line, the gas escaping via the second void, which is vented. A meter connection to the first void of each pair is supplied to a differential pressure meter and/or a device that converts a differential pressure to an electrical signal for remote readout or the like.

21 Claims, 5 Drawing Figures

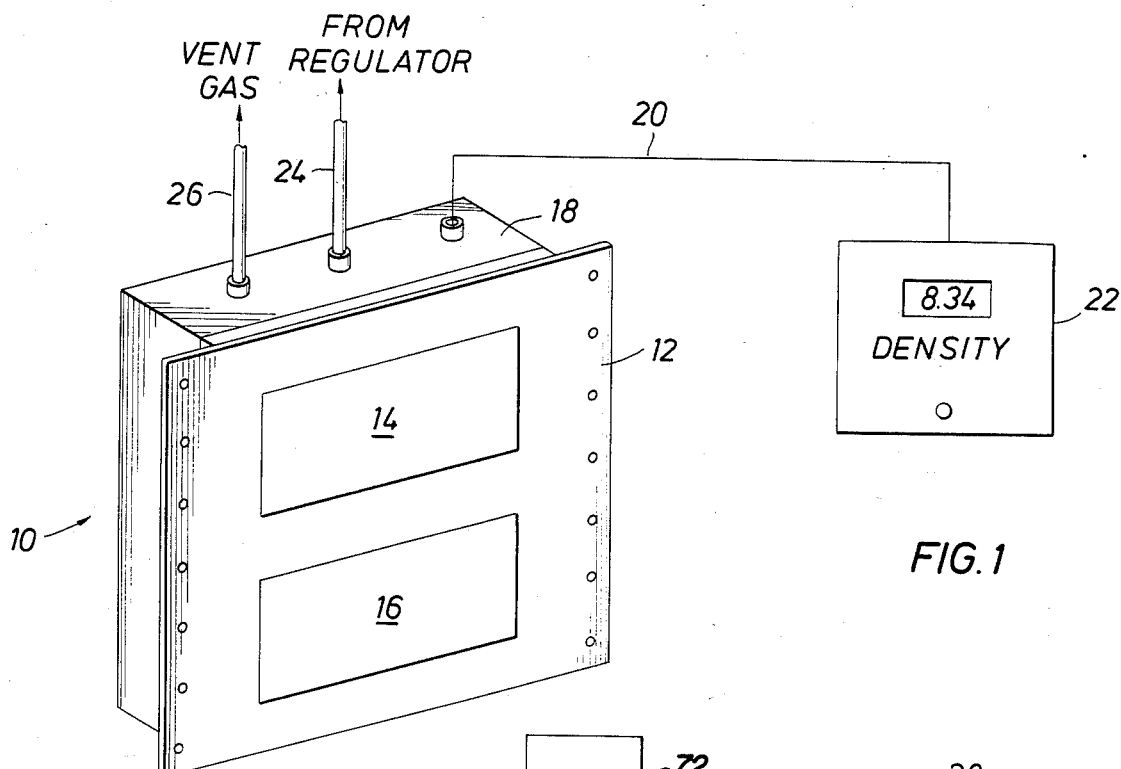
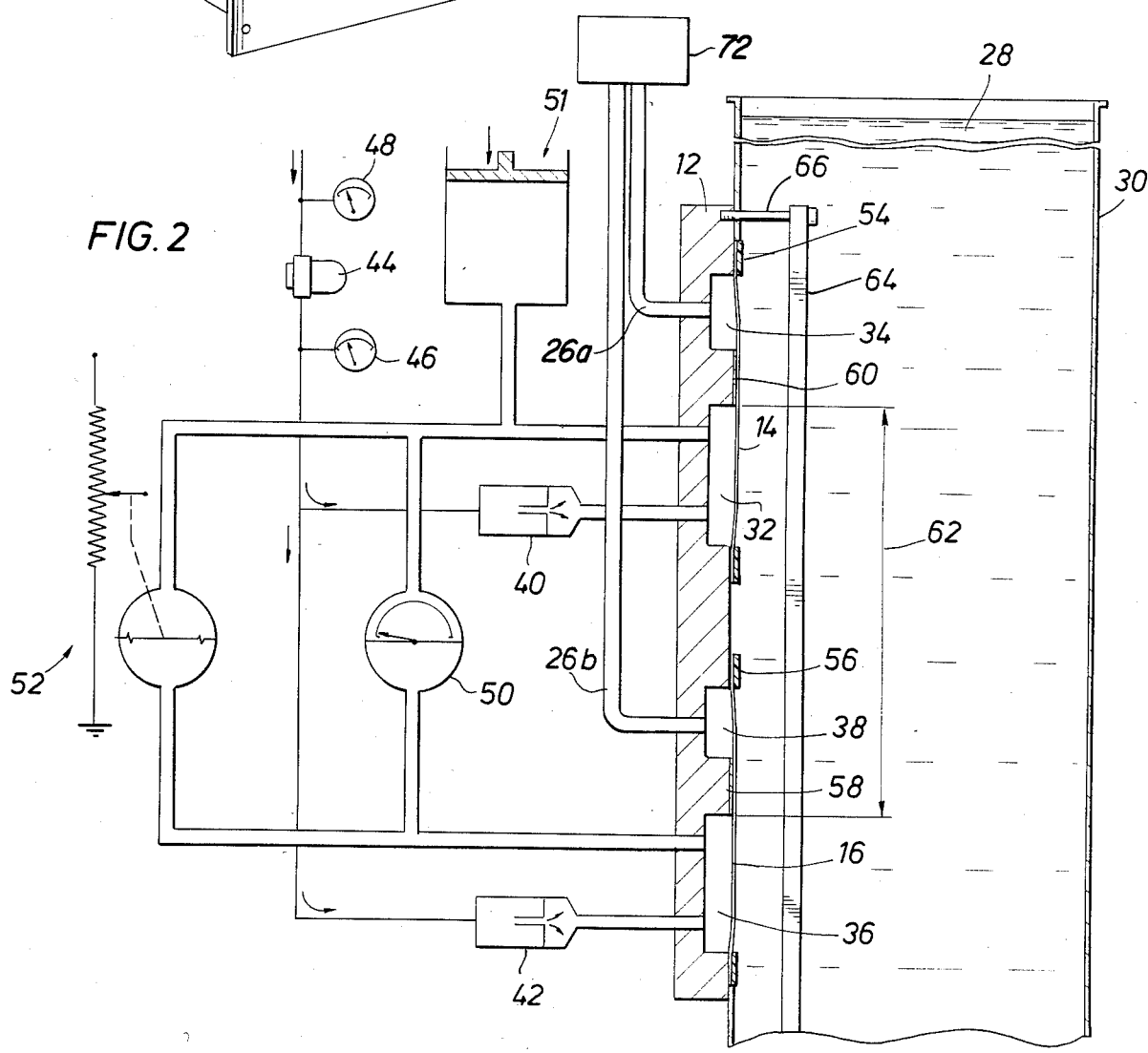

LIQUID DIFFERENTIAL PRESSURE MEASUREMENT USING A VERTICAL MANIFOLD

BACKGROUND OF THE INVENTION

1. Field of the Invention

This invention relates to liquid pressure measurements and more particularly, to related density measurements by measuring the difference in pressure in a quantity of liquid between a first and second vertical location.

2. Description of the Prior Art

Huge fluid systems, such as exemplified by mud systems of an oil well drilling operation, often need to be closely and continuously monitored for variation in conditions. By monitoring such parameters as the density or change of density over a period of time of such a system, it is possible to deduce what is occurring with the environment or the procedure supported by the liquid system. For example, the infusion of gas or salt water from the formation will change the density of the liquid in the system. Likewise, the settling, addition or extraction of suspended particulates will also cause a resulting change in the fluid density of the system.

A popular procedure for measuring density of liquids uses a sampling densitometer. Although accurate and convenient in some contexts, it necessarily only provides sampling of a limited quantity of the liquid, which may not be homogeneous throughout the larger quantity from which the sample is drawn. Further, such a measurement is a measurement of intermittent conditions and does not provide a continuous readout.

A more suitable procedure for measuring density or changes in density of a large liquid system is provided by the employment of a pressure differential gauge, the pressure sampling being taken at two different vertical locations within the liquid quantity. One of the best and most reliable of such devices is disclosed in patent application Ser. No. 06/371.789, "Method and Apparatus for Gauging Liquid Filled Tanks", filed Apr. 26, 1981 by the same inventor, now U.S. Pat. No. 4,446,730 which is incorporated herein by reference for all purposes.

It has heretofore been believed that the pressure-sensitive element or elements, usually in the form of a diaphragm or diaphragms employed in a pressure sampling device, were necessarily preferably oriented to be in horizontal planes. This is because the pressure at a given vertical location within a quantity of liquid is at the same pressure level. Therefore, if the sampling diaphragm were oriented horizontally, it would effectively be measuring the pressure in that horizontal plane. On the otherhand, a vertically oriented diaphragm would cause sampling to occur at some inexact pressure location between the top and bottom of the diaphragm. That is, the top of the diaphragm would be at one pressure and the bottom of the diaphragm would be at a different pressure. This is because the pressure varies with depth of the liquid. Due to the flexing characteristics of the diaphragm, the actual pressure level would not reliably be in a centered position between top and bottom, but at a location that even varies with the amount of pressure in contact therewith.

However, it may be recognized that liquid systems, such as a mud system, that are best monitored by continuously measuring and indicating devices, are by definition dynamic, ever-changing systems, as opposed to static or calm systems. Such systems are often turbulent. When confined, the swirling turbulence in the vertical direction is much greater than the wave action from side to side. Hence, a horizontally-oriented diaphragm is subject to such predominant turbulence, causing fluctuating and even false readings to result.

Although it is possible to place a barrier in front of a horizontal diaphragm to eliminate some of the turbulent action from affecting the pressure sensing, such a barrier is unsatisfactory in the presence of sediment or solid particles. This is because such sediment will build up on the barrier and, in time, if sufficiently close to the diaphragm to be an effective shield against turbulence, will even accumulate to the extent that it will prevent free movement of the diaphragm. This will cause false and unacceptable readings to result.

Therefore, it is a feature of the present invention to provide an improved device for measuring pressure in a quantity of liquid wherein one or more vertically oriented membranes are used, but in such a manner that the pressure is measured at precise vertical location(s).

It is another feature of the present invention to provide an improved device for measuring the difference in pressure in a quantity of liquid between a first and a second vertical location wherein vertically oriented membranes are used, but in such a manner that the pressure differential is precise with respect to such locations.

It is yet another feature of the present invention to provide an improved device for pressure measurement in a liquid employing vertically oriented membranes that are protectable from turbulence by a vertical barrier which is not susceptible to sediment build-up in the manner of a horizontally oriented barrier.

SUMMARY OF THE INVENTION

The illustrated preferred embodiment of the invention pertains to apparatus for monitoring the difference in pressure at a first vertical location in a quantity of liquid compared with the pressure at a second vertical location in the liquid. A manifold is employed having a pair of voids or openings at each of the locations on the liquid side thereof. The upper void has a flow-through passage to the external side of the manifold and the lower void has two flow-through passages to the external side of the manifold. A regulated supply of gas or air furnishes such gas or air through an external restrictor to the lower void through one of its flow-through passages. A second flow-through passage of the lower void is connected to a pressure differential meter. The upper void is vented through its flow-through passage preferably to the atmosphere. The entire liquid-side of the pair of voids or openings is sealed by a common vertical flexible membrane tightly pressing against the horizontal wall or fence between the voids.

When the pressure from the restrictor to the lower void overcomes the pressure head of the liquid applied to the membrane at the edge of the fence at the top of the lower void, then the membrane moves outwardly from the fence and the gas is vented via the second void and its flow-through passage to the atmosphere. Hence, the gas pressure to the meter connected to the second flow-through passage to the lower void is a measure of the gas or air pressure at the horizontal fence edge when this event occurs.

The other or differential side of the meter is similarly connected to a flow-through passage connected to the lower void of the other pair. Hence, in the same manner, the gas pressure is a measure of the pressure at the edge of the fence at the top of its lower void. A surge eliminator is connected in the connecting line to one side of the meter to compensate for differences in length of lines from the respective restrictors and void pairs connected to the meter.

BRIEF DESCRIPTION OF THE DRAWINGS

So that the manner in which the above-recited features, advantages and objects of the invention, as well as others which will become apparent, are attained and can be understood in detail, more particular description of the invention briefly summarized above may be had by reference to the embodiment thereof which is illustrated in the drawings, which drawings form a part of the specification. It is to be noted, however, that the appended drawings illustrate only a preferred embodiment of the invention and are, therefore, not to be considered limiting of its scope for the invention may admit to other equally effective embodiments.

In the Drawings:

FIG. 1 is an isometric representation of a preferred embodiment of the manifold and related parts of the invention.

FIG. 2 is a schematic representation of a preferred embodiment of the invention.

DESCRIPTION OF THE PREFERRED EMBODIMENTS

Figure 4:
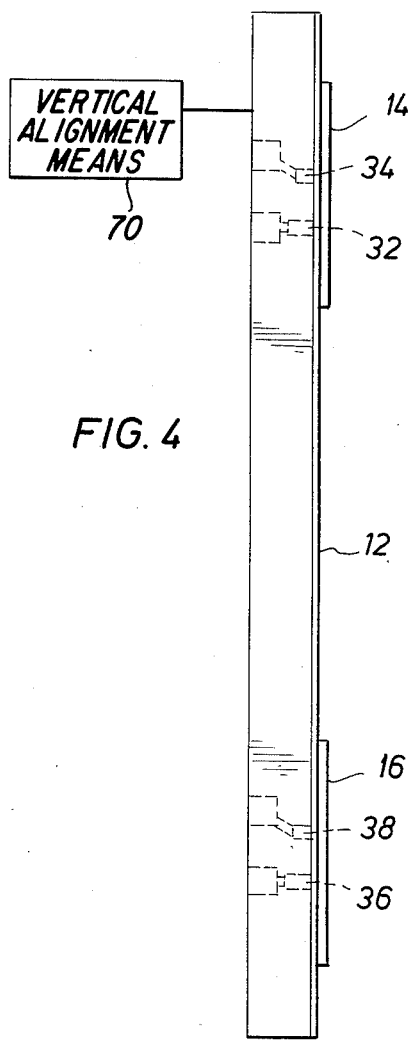
FIG. 4 is a side view of the embodiment shown in FIG. 3.

Now referring to the drawings and first to FIG. 1, apparatus 10 is shown in an isometric view for connection into a window or sidewall of a container filled with a large volume of liquid. Plate or manifold 12 is suitably provided with bolt holes for mounting purposes along its two vertical flange sides. Openings or voids to be described below are covered by two thin membranes 14 and 16, one in a suitable vertical location over the other. Normally, this distance is about 1.0 foot. These membranes are made of a non-elastomer material, typically Mylar. A housing for the pneumatic and electronic components of the system to be described are housed in housing 18 attached or hinged by any convenient means well known in the art. Electrical connection 20 to meter 22 provides a readout of differential pressure in density units of measurement. Pneumatic connection 24 provides a connection to a pressure regulator and connection 26 from housing 18 provides a vent to the atmosphere or, alternatively, to a closed container for purposes hereafter described.

Now referring to FIG. 2, a large quantity of liquid 28 is shown in container or tank 30. Typically this may be a holding tank for the mud of a mud system used in an oil well drilling operation. Bolted to one side of the tank in a window, or comprising the side thereof, is manifold 12, which is shown in cross-section. Two pairs of vertically separated voids are included in manifold 12 disposed on the internal or liquid side of the manifold. The upper pair of voids comprise lower void 32 and upper void 34. The bottom pair of voids comprise lower void 36 and upper void 38. Voids 32 and 34 are respectively substantially identical to voids 36 and 38.

The voids are all provided with flow-through passages to the external side of the manifold. It may be observed that the lower void 32 and 36 of each pair is provided with two flow-through passages and the upper void of each pair is provided with a single flow-through passage. The flow-through passage of the upper voids 34 and 38, respectively, are connected to connections 26a and 26b, which are vented to the atmosphere in the preferred embodiment. These connections 26a and 26b may be joined together as vent connection 26 shown in FIG. 1. Alternatively, connections 26a and 26b may be vented together or separately to a common closed container 72.

The lower flow-through connection to voids 32 and 36, respectively, are connected to flow restrictors 40 and 42, respectively. A preferred means of flow restriction is a very small diameter tubing, such as used to fabricate hypodermic needles. It may be seen that the restrictive flow of gas is reduced to approximately 0.25 standard cubic foot per hour (scfh) when provided with regulated pressure at its input side at approximately 25 psig. The input side of restrictors 40 and 42 receive a regulated supply of gas or air via connections leading from regulator 44, as metered by meter 46. The gas supply input to the regulator is typically approximately 100 psig as indicated on meter 48 connected to the unregulated side of the regulator.

Returning to the connections to the manifold, the upper flow through passages to voids 32 and 36 respectively are connected to opposite sides of a pressure differential meter 50, which may be calibrated to read directly in liquid density units. Marion Gauge Company manufactures such a meter.

Alternatively, or in addition, the outlet connections from voids 32 and 36, respectively, can also be connected to a pressure-to-electrical conversion device 52, which may be identical in configuration to the device shown in FIG. 1 of U.S. Pat. No. 4,446,730.

One of the output lines from voids 32 and 36 connected to devices 50 and 52 is also connected to surge eliminator 51, which is conveniently an adjustable piston-and-cylinder arrangement for increasing or decreasing the pressure in the line to which it is connected for a purpose described below.

The tank side or liquid side of the manifold includes a membrane covering over each pair of voids. The manifold is securely attached, such by a suitable bonding material around each pair of voids to form a tightly pressing membrane covering these voids. It may be seen in FIG. 2 that membrane 14 is connected above void 34 to the surface of the manifold and below void 32 to the surface of the manifold. It is not attached to the horizontal wall or fence between the voids but is tightly pressed thereagainst for a purpose to be explained. In like fashion, membrane 16 is secured to the manifold to cover voids 36 and 38. Membrane 16 is not attached to the horizontal fence between void 36 and 38. Preferably, the surface of the manifold, and particularly the fences just described, are made of non-corrosive materials, such as stainless steel, suitable plastic such as Delrin or the like. The liquid may be highly corrosive and such protection of surfaces prolongs the life of the parts and further protects the surfaces from corrosive and errosive effects caused by the pressurized gas.

Now referring to the operation of the device just described, the input supply of gas is established so that the flow pressure from restrictors 40 and 42 are each between 0.1–1 scfh, preferably 0.25 scfh. It will be seen that the gas into void 36 from restrictor 42 flows through the other passageway connected to void 36 to meter 50. However, when the pressure inside void 36 builds up sufficiently to overcome the pressure head of liquid 28 against the external surface of membrane 16, it will cause membrane 16 to flex slightly at fence 58 between the voids 36 and 38. Such slight flexing permits gas to escape through void 38 and out exhaust vent 26b. Hence, the pressure inside void 36 only builds up to the extent that it represents the pressure which is overcome as applied against membrane 16. Specifically, the horizontal line of contact that membrane 16 has with the top edge of void 36 is the vertical location of the pressure being measured.

In like fashion, input pressurized gas from restrictor 40 is applied to void 32 so as to move the covering membrane 14 slightly outwardly from fence 60 between void 32 and 34. Pressurized gas escapes at the edge of the fence which is at the top of void 32 out through void 34 and vent exhaust 26a. Hence the pressure differential which is supplied to meter 50 and/or device 52 is the distance between the edges of the fences just described, represented by numeral 62. In one usual operating condition for the manifold just described, this distance 62 is 1.0 foot.

It may be recognized that the connections from restrictor 40 to void 32 and then from void 32 to meter 50 may not be the same volume as the connection path from restrictor 42 to void 36 and from void 36 to the opposite side of meter 50. This means that when there is a change of pressure in the liquid, the needle or indicator of meter 50 may fluctuate momentarily because of the differences in volumes in these connection paths. This needle oscillation effect is overcome by establishing a compensating volume to one of these paths, such as by surge eliminator 54. The amount of volume added by use of the surge eliminator is readily determined by merely watching the meter as it responds to surges and increasing or decreasing the surge eliminator volume until such fluctuations stop.

Hence, it may be seen that the surge eliminator feature just described produces an equal volume response downstream of each flow restrictor. It is common for a differential pressure meter 50 or an electrical conversion device 52 to experience a volume difference in high side to low side as much as 5 to 1. Therefore, a quick increase in common-mode pressure on both membranes 14 and 16 fills one side much faster than the other side, thereby producing a surge in output reading, up or down, depending on the direction of volume unbalance. By adjusting the effective volume with the surge eliminator, common-mode pressure surges do not affect the outputs of meter 50 or device 52.

Figure 3:
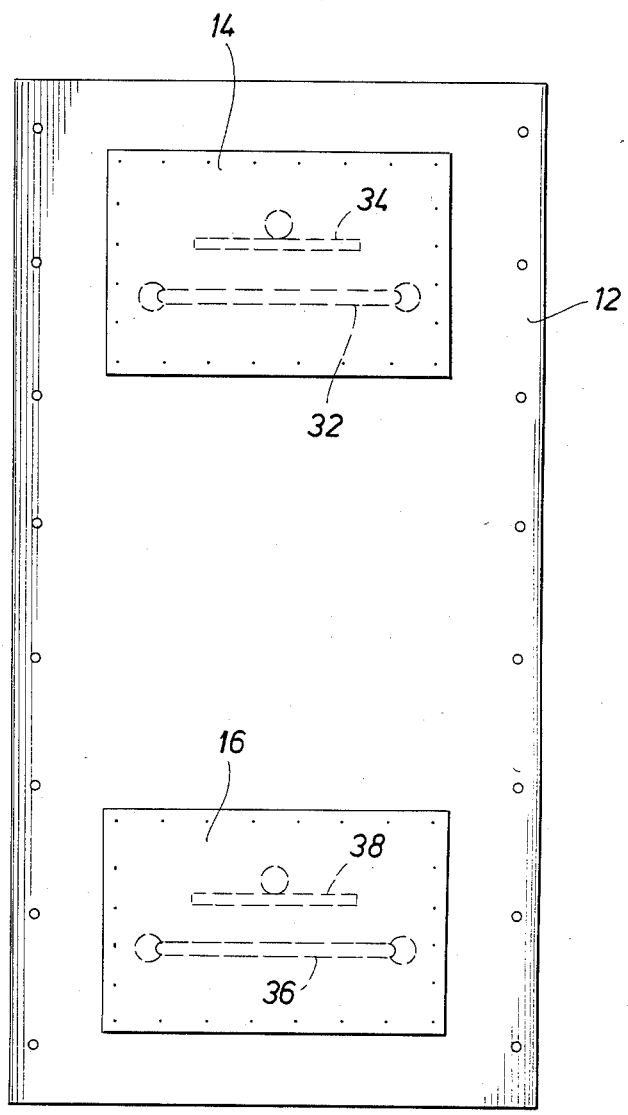
FIG. 3 is a front view of a preferred embodiment of the manifold portion of the invention.
Figure 5:
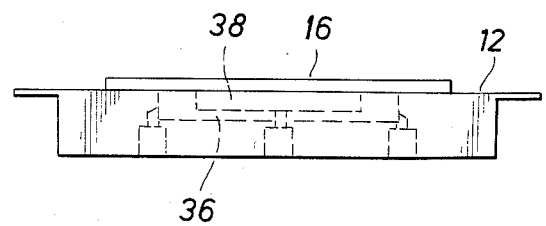
FIG. 5 is a bottom view of the preferred embodiment of the invention shown in FIG. 3.

Now referring to FIGS. 3, 4 and 5, it may be seen that the preferred configurations of voids 32, 34, 36 and 38 are elongated slots. The two flow-through passages to void 32 and 36, respectively, may conveniently be at the two ends of the slot as shown in FIGS. 3, 4 and 5, rather than in one above the other as schematically represented in FIG. 2. The flow-through passage to voids 34 and 38, respectively, may be just above their respective slots, although this position is not critical. It will be seen that the long horizontal edge of the slots, and particularly slots 32 and 36, provide the fence edge which was described in connection with distance 62.

It may be seen that the non-elastomer membranes which have been referred to are conveniently bonded either continuously or at a plurality of closely positioned bonding points as represented in the drawings. Although the two membranes are some distance apart, as is normally the case, it is possible to use a single sheet to make both membranes. However, because the distance is normally much too great to make this economically attractive, two separate membranes are normally employed.

Now returning to FIG. 2, it is possible to readily protect the surfaces of the membrane from surges that normally occur in liquid 28 by putting a barrier or shield 64 in front of these membranes. These barriers may be conveniently secured by standoffs 66 in conventional fashion. It may be observed that particulates that settle from the solution will not build up on the surface of the shield so as to interfere with the operation of the membranes, but instead will fall to the bottom of the tank or container and free from interfering with operation of the membranes.

Although the manifold has been discussed above with respect to being a part of one side of a compartment or tank holding liquid 28, alternatively it may be conveniently positioned independently of a sidewall so long as the membranes themselves on one side are subject to pressure from liquid 28 in the manner just discussed. It is not uncommon for large liquid tanks to be included in some kind of a vehicle, such as a large ship, which may sway back and forth. In order to keep the manifold aligned in a vertical position, it is also possible to mount such manifold with convenient gimbal connections 70 or otherwise so that it remains vertical in spite of the fact that the container itself may deviate from vertical alignment by quite some distance as it sways with the ship.

While a particular embodiment of the invention has been shown and described, and modifications or alternatives have been discussed above, it will be understood that the invention is not limited thereto since modifications may be made and will become apparent to those skilled in the art. For example, it may be desirable to connect the output as part of a regulation system to retain the density within certain predetermined limits, if desired.

What is claimed is:

1. Apparatus for measuring the difference in pressure in a quantity of liquid between a first and second vertical location therein, comprising:
   a manifold with a first side exposed to the liquid, said first side having a first pair of voids separated by a first fence at a first vertical location between said first pair of voids and a second pair or voids separated by a second fence at a second vertical location between said second pair of voids, said second location being above said first location, a first one of each pair of voids having two flow-through passages to the second side of said manifold and the second one of each pair of voids being vented,
   a supply of pressurized gas,
   a first flow restrictor connected to one of said flow-through passages of said first one of said first pair of voids and to said pressurized gas supply,
   a second flow restrictor connected to one of said flow-through passages of said first one of said second pair of voids and to said pressurized gas supply,
   meter means sensitive to pressure difference having a first connection to the second one of said flow-through passages of said first one of said first pair of voids and a second connection to the second one of said flow-through passages of said first one of said second pair of voids, a first flexible membrane vertically tightly covering said first pair of voids and contacting said first fence therebetween, a second flexible membrane vertically tightly covering said second pair of voids and contacting said second fence therebetween, gas pressure from said first restrictor causing said first membrane to move slightly outwardly at said first fence at the hydrostatic pressure of the liquid applied thereagainst to vent the gas built up in said first void through said second void of said first pair of voids, said first void pressure being applied to said meter, gas pressure from said second restrictor causing said second membrane to move slightly outwardly at said second fence at the hydrostatic pressure of the liquid applied thereagainst to vent the gas built up in said first void through said second void of said second pair of voids, said first void pressure being applied to said meter to result in a pressure differential reading of the hydrostatic liquid pressures between said first fence and said second fence.

2. The apparatus in accordance with claim 1, wherein said manifold at the second one of each pair of voids includes a flow-through passage vented to the atmosphere.

3. The apparatus in accordance with claim 1, wherein the second one of each pair of voids is vented to a common closed container.

4. The apparatus in accordance with claim 1, and including a container for holding the quantity of liquid subject to pressure difference measurement.

5. The apparatus in accordance with claim 1, wherein the supply of pressurized gas is approximately 25 psig.

6. The apparatus in accordance with claim 1, wherein the restricted flow of gas from said first flow restrictor and from said second flow restrictor is between approximately 0.1–1 standard cubic foot per hour.

7. The apparatus in accordance with claim 6, wherein the restricted flow of gas is approximately 0.25 standard cubic foot per hours.

8. The apparatus in accordance with claim 1, wherein said membranes comprises a non-elastomer material.

9. The apparatus in accordance with claim 8, wherein said non-elastomer material is Mylar.

10. The apparatus in accordance with claim 1, wherein said first membrane contacts said first fence in a first horizontal line at the top of said first void of said first pair of voids and said second membrane contacts said second fence in a second horizontal line at the top of said first void of said second pair of voids, said pressure differential reading being between said first horizontal line and said second horizontal line.

11. Apparatus in accordance with claim 1, and including
a surge eliminator connected to said first connection or said second connection to said meter for compensating for the difference in volumes from said first restrictor through said first void of said first pair of voids through said first connection to said meter and from said second restrictor through said first void of said second pair of voids through said second connection to said meter.

12. Apparatus in accordance with claim 10, wherein said surge eliminator is connected to said second connection.

13. Apparatus in accordance with claim 10, wherein said surge eliminator includes an adjustable piston-and-cylinder for varying the amount of volume in said connection to which said surge eliminator is connected.

14. Apparatus in accordance with claim 10, wherein said surge eliminator is connected to said connection of said meter that is at the lowest pressure, said surge eliminator including a piston-and-cylinder for increasing the amount of volume in said connection to compensate for the volume difference in said path lengths.

15. Apparatus in accordance with claim 1, and including vertical alignment means for ensuring said first pair of voids is vertically in alignment with said second pair of voids.

16. Apparatus in accordance with claim 1, wherein the quantity of liquid subject to pressure difference measurement is held by a container that is subject to swaying, and including vertical alignment means for ensuring said first pair of voids is vertically in alignment with said second pair of voids while said container sways.

17. Apparatus in accordance with claim 15, wherein said vertical alignment means includes level suspension means.

18. The apparatus in accordance with claim 1, wherein said meter is calibrated for directly reading the density of the liquid.

19. The apparatus in accordance with claim 1, and including a protective shield spaced apart from said first membrane and said second membrane to suppress turbulence of the liquid from falsely affecting the pressure difference measurements.

20. The apparatus in accordance with claim 1, wherein said manifold is non-corrosive.

21. The apparatus in accordance with claim 1, wherein said meter means includes pressure-to-electrical conversion means.

* * * * *